United States Patent [19]

Boici

[11] 4,012,505

[45] Mar. 15, 1977

[54] ANALGESIC SUBSTANCE DERIVED FROM THE HELLEBORUS PLANT AND METHOD OF MAKING SAME

[75] Inventor: Vasile Boici, Timisoara, Romania

[73] Assignee: Intreprinderea de Medicamente Terapia, Romania, Cluj-Napoca, Romania

[22] Filed: Nov. 26, 1975

[21] Appl. No.: 635,636

[52] U.S. Cl. .............................................. 424/195
[51] Int. Cl.$^2$ ...................................... A61K 35/78
[58] Field of Search .................................. 424/195

[56] References Cited
OTHER PUBLICATIONS

The National Dispensatory (Fifth Ed.) 1896, Lea Brothers & Co., N.Y., pp. 808–810.
The Dispensatory of the U.S.A. 24th Ed., (1947) J. B. Lippencott Co., Phila. Pa., pp. 1475 & 1476.

*Primary Examiner*—Donald B. Moyer
*Attorney, Agent, or Firm*—Karl F. Ross; Herbert Dubno

[57] ABSTRACT

An analgesic substance with selective "loco dolenti" action. The pharmaceutical substance is obtained by extracting the roots and stems of the Helleborus, the extract being recovered and subjected to ultrasonic radiation which has a stabilizing effect.

3 Claims, No Drawings

ANALGESIC SUBSTANCE DERIVED FROM THE HELLEBORUS PLANT AND METHOD OF MAKING SAME

The present invention relates to an analgesic, substance derived from the Helleborus plant by alcoholic extraction and to a method of making this substance.

Various analgesic pharmaceutical substances have been used heretofore as derived from synthetic or natural materials, including plant extracts. The most widely known substances are phenacetine, phenasone derivatives pyrasolidines, dimethylphenylpyrasoline and acetylsalicylic acid (Aspirin) which can be used individually or together and which act upon the central nervous system or the nerve paths themselves.

Alkaloids extracted from Aconitum plant tubers also have analgesic effects and are effective on the central nervous system.

For topical application "loco dolenti" such compounds can be used in solution or ointments and the latter may contain nicotinic derivatives (e.g. benzylic ester of nicotinic acid) and salicylic acids with or without plant extracts such as Capsicum extracts.

Most of the aforementioned antialgic compounds have limited utility, long treatment times and large dosage requirements. They have short effective durations and significant side effects in that they cannot be tolerated readily. In addition, they must be made by complex manufacturing processes.

It is the object of the invention to provide an improved analgesic pharmaceutical substance and method of making same.

This object is achieved by extracting the roots and stems of the Helleborus species of the botanical family Ranunculaceae with alcohol and recovering the pharmaceutical substance from the alcoholic extract. The pharmaceutical is found to be effective loco dolenti as an analgesic compound and acts as a vasodilator, antiseptic and anabolic agent capable of use for a variety of algias with no significant contraindications, or toxicity and shorter treatment time than anti-algic compounds known heretofore.

According to the invention the pharmaceutical substance is prepared by extracting the roots and stems of the Helleborus plant with ethyl alcohol in a ratio of one part of the botanical material to 2-3 parts of ethyl alcohol at room temperature, treating the extract with concentrated hydrochloric acid in a ratio of one part of the acid to 10 parts of the extract, filtering the resulting precipitate from the solution and de-coloring the filtrate with active carbon.

The filtrate is then neutralized with 10% sodium hydroxide to a pH of 6.5-7 and diluted with water to obtain an isotonic solution.

According to the invention this solution is then subjected to ultrasonic radiation at a rate of $0.005w/cm^2$ for 1 to 6 minutes to yield the pharmaceutical agent.

The product is a vasodilator with long lasting effectiveness loco dolenti and with vasotonic action, when administered for the treatment of headaches, has a prolonged and almost instantaneous relief, and induces a selective analgesic effect at loci of maximum pain. It has an anabolic and spasmolytic action and has been found to re-establish normal physiological functions of organs and parts thereof subject to algesic attack.

The pharmaceutical is not toxic, can be used in small doses and with high tolerance without particular side effects. It has not been found to be significantly counterindicated, does not induce local infection and shortens the period of temporary functional incapacity and allows recovery of chronic sufferers from the disorder.

SPECIFIC EXAMPLE

The stems and roots of the Helleborus are macerated for 36 hours in ethyl alcohol in a ratio of one part of plant material to 2-3 parts of the solvent at room temperature and the raw extract is recovered.

The raw extract is treated with one part of pure concentrated hydrochloric acid to 10 parts of extract and heated to boiling for 3 minutes and cooled. The resulting precipitate is allowed to settle out and active carbon is added to decolor the decantate. The solution is filtered and the precipitate is discarded.

The filtrate is neutralized with 10% sodium hydroxide to a pH 6.5-7 and an additional quantity of active carbon is added. The solution is filtered and it is observed that the filtrate has a pH of 4.5-6.

Depending upon the amount of sodium chloride formed by the neutralization step, the solution is completed with distilled water to obtain a sodium chloride concentration corresponding to that of an isotonic solution.

The solution is passed through filter paper to remove the larger solids and then through a G-5 filter plate and is irradiated with ultrasonic radiation at a level of $0.005w/cm^2$ for 3 minutes. The liquid composition thus obtained is used as injectable solution or as the active material in tablets, coated pills, cachets, topically applicable solutions, suppositories and ointments.

I claim:

1. A method of making a locally applicable analgesic composition which comprises the steps of:
   a. extracting stems and roots of the Helleborus species of one Ranunculaceae genus with alcohol in a ratio of the part of the plant material to 2-3 parts of the alcohol at about room temperature to form a raw extract;
   b. treating said raw extract with concentrated hydrochloric acid in a ratio of one part of the acid to 10 parts of the extract, thereby forming a precipitate therein;
   c. decoloring the filtrate resulting from the separation of the liquid from the precipitate formed in step (b) with active carbon and neutralizing the decolored filtrate to a pH of about 6.5 to 7 with about 10% sodium hydroxide; and
   d. diluting the solution formed in step (c) with distilled water to bring the sodium chloride concentration thereof to a substantially isotonic concentration, thereby consituting of said solution, said composition.

2. The method defined in claim 1 wherein said composition is irradiated with ultransonic radiation in doses of $0.005w/cm^2$ for 1 to 6 minutes.

3. A method of treating an algesia condition comprising the step of applying to the skin an effective amount of the composition made by the method of claim 1.

* * * * *